(12) United States Patent
Kumagai et al.

(10) Patent No.: US 8,244,496 B2
(45) Date of Patent: Aug. 14, 2012

(54) FUEL VISCOSITY DETECTION APPARATUS

(75) Inventors: Akio Kumagai, Susono (JP); Takashi Hotta, Susono (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 356 days.

(21) Appl. No.: 12/674,788

(22) PCT Filed: May 18, 2009

(86) PCT No.: PCT/JP2009/059114
§ 371 (c)(1),
(2), (4) Date: Feb. 23, 2010

(87) PCT Pub. No.: WO2010/134150
PCT Pub. Date: Nov. 25, 2010

(65) Prior Publication Data
US 2011/0130979 A1    Jun. 2, 2011

(51) Int. Cl.
*G06F 19/00* (2006.01)
(52) U.S. Cl. ......................................... 702/150
(58) Field of Classification Search .................. 702/150
See application file for complete search history.

(56) References Cited

U.S. PATENT DOCUMENTS

| 4,252,097 A | 2/1981 | Hartford et al. |
| 5,776,222 A * | 7/1998 | Kopylov et al. ............... 65/384 |

FOREIGN PATENT DOCUMENTS

| JP | 55-007996 A | 1/1980 |
| JP | 09-287540 A | 11/1997 |
| JP | 11-125134 A | 5/1999 |
| JP | 2004-144024 A | 5/2004 |
| JP | 2004-239196 A | 8/2004 |

OTHER PUBLICATIONS

International Search Report for PCT/JP2009/059114, dated Jul. 28, 2009, 3 pages.

* cited by examiner

*Primary Examiner* — Tung S Lau
(74) *Attorney, Agent, or Firm* — Sughrue Mion, PLLC (57) ABSTRACT

An object of the present invention is to estimate a viscosity of a fuel with high accuracy at all times, irrespective, for example, of fuel properties or conditions of deterioration with time.

An internal combustion engine 10 includes a fuel pump 32 for supplying an injection valve with fuel in a tank 24. An ECU 40 detects a transition time t that begins when a drive signal is outputted to the fuel pump 32 and ends when the pump enters a steady operating state. At a start of the fuel pump 32, the higher the viscosity of the fuel, the longer the transition time t tends to be. The ECU 40 therefore detects the viscosity of the fuel based on a deviation $\Delta t$ between the transition time t and a reference time t0. If, for example, a biofuel is used, therefore, the latest viscosity can be accurately detected at all times even with the viscosity of the fuel fluctuating depending on, for example, properties or a condition of deterioration with time of the fuel, and the detection result can be incorporated in, for example, correction of a fuel injection pressure.

6 Claims, 8 Drawing Sheets

| Viscosity (mm²/s) | Correction value of Injection pressure (Mpa) | | |
|---|---|---|---|
| 0〜10 | 0.01 | 0.02 | 0.04 |
| 11〜20 | 0.03 | 0.03 | 0.04 |
| 21〜30 | 0.05 | 0.06 | 0.07 |
| …… | …… | …… | …… |
| | 0〜40 | 40〜80 | 80〜 |
| | Fuel injection pressure (MPa) | | |

FUEL VISCOSITY DETECTION APPARATUS

TECHNICAL FIELD

The present invention relates to a fuel viscosity detection apparatus suitably used in, for example, a power drive engine operative with fuel.

BACKGROUND ART

A known apparatus is arranged to estimate viscosity of fuel and, based on the estimated value, control a discharge quantity of a fuel pump, as disclosed, for example, in Patent Document 1 (JP-A-9-287540). In the known art, the viscosity and concentration of the fuel is estimated according to, for example, temperature or properties of the fuel and the discharge quantity of the fuel pump is calculated from these estimated values.
Prior Art Documents
Patent Document
    Patent Document 1: JP-A-9-287540

DISCLOSURE OF THE INVENTION

Problem to be Solved by the Invention

In accordance with the above-described known art, the viscosity is estimated according to, for example, the temperature or properties of the fuel. A case in which a type of fuel, for example, biofuel that gradually changes its viscosity as a result of deterioration with time, or one having properties not expected during designing is used, however, poses a problem in that the viscosity of the fuel cannot be accurately estimated. If the viscosity of fuel cannot be accurately estimated, an error tends to occur in a fuel injection amount, resulting, for example, in possible aggravation of exhaust emissions and increase in deposits.

The present invention has been made to solve the foregoing problem and it is an object of the present invention to provide a fuel viscosity detection apparatus that can estimate fuel viscosity with high accuracy at all times, irrespective, for example, of fuel properties or conditions of deterioration with time.

Means for Solving the Problem

A first aspect of the present invention is a fuel viscosity detection apparatus, comprising:
    an electrically operated pump for drawing and delivering fuel;
    operating state change means for applying to the electrically operated pump a factor for changing an operating state of the electrically operated pump from the first steady state to the second steady state;
    transition time detection means for detecting a period of time that begins when the factor is applied to the electrically operated pump and ends when an actual operating state becomes the second steady state as a transition time between the steady states; and
    viscosity calculation means for calculating a viscosity of the fuel based on the transition time.

In a second aspect of the present invention, the fuel viscosity detection apparatus according to claim 1, further comprising:
    detection means for detecting at least one of parameters of current, voltage, and electric power supplied to the electrically operated pump and an output speed of the electrically operated pump,
wherein the transition time detection means detects a period of time that begins when the factor is applied to the electrically operated pump and ends when the parameter becomes a value associated with the second steady state as the transition time.

In a third aspect of the present invention, the fuel viscosity detection apparatus according to claim 1 or 2,
wherein the operating state change means includes pump start means for changing the operating state of the electrically operated pump from a stationary state that is the first steady state to a steady operating state that is the second steady state by outputting a drive signal to the electrically operated pump; and
    the transition time detection means includes start time detection means for detecting a period of time that begins when the drive signal is outputted and ends when the electrically operated pump enters the steady operating state as the transition time.

In a fourth aspect of the present invention, the fuel viscosity detection apparatus according to any one of claims 1 to 3,
wherein the operating state change means includes pump stop means for changing the operating state of the electrically operated pump from a steady operating state that is the first steady state to a stationary state that is the second steady state by turning off the drive signal to the electrically operated pump; and
    the transition time detection means includes stop time detection means for detecting a period of time that begins when the drive signal is turned off and ends when the electrically operated pump stops as the transition time.

In a fifth aspect of the present invention, the fuel viscosity detection apparatus according to claim 1 or 2, further comprising:
    variable fuel pressure means for variably setting a pressure of the fuel delivered from the fuel pump,
    wherein the operating state change means changes the operating state of the electrically operated pump from the first steady state to the second steady state by changing a pressure setting value of the variable fuel pressure means; and
    the transition time detection means detects a period of time that begins when the pressure setting value is changed and ends when the electrically operated pump enters the second steady state as the transition time.

In a sixth aspect of the present invention, the fuel viscosity detection apparatus according to any one of claims 1 to 5, further comprising:
    notification means for notifying a state in which the viscosity of the fuel falls outside a predetermined reference range.

Effects of the Invention

According to the first invention, the operating state change means can change the operating state of the electrically operated pump from the first steady state to the second steady state by applying an external factor to the pump. At this time, the transition time detection means can detect the transition time it takes to change the operating state. The transition time changes according to the viscosity of the fuel. Thus the viscosity calculation means can calculate the viscosity of the fuel based on the transition time. The viscosity of the fuel can therefore be accurately and easily detected by simply controlling the electrically operated pump without having to install, for example, a viscosity sensor. Additionally, the latest viscosity can be obtained at all times with high accuracy at any timing of pump operation, whether during starting, stopping, or operating, according to the factor applied to the pump. The detection result can then be incorporated in control of various types. Consequently, for example, a fuel injection pressure can be appropriately controlled according to the viscosity even with, for example, biofuels whose viscosity tends to change easily.

According to the second invention, the transition time detection means can detect the transition time when at least one of the parameters of the current, voltage, and electric power supplied to the electrically operated pump and the output speed of the pump becomes a value associated with the second steady state. This eliminates a mandatory need for detecting the speed of the pump. Entry of the pump in the steady state can therefore be reliably detected, regardless of whether, for example, a rotation sensor is used or not, thus achieving a simplified system and cost reduction.

According to the third invention, when, for example, an internal combustion engine is to be started, the viscosity of the fuel can be detected by using an operation to start the electrically operated pump. Consequently, even if the viscosity of the fuel changes due to, for example, parking for a long time, the latest viscosity at the start of operation can be detected and the detection result can be promptly incorporated in control of various kinds. This enhances startability of the internal combustion engine and improves a combustion state immediately following the start.

According to the fourth invention, when, for example, the internal combustion engine is to be stopped, the viscosity of the fuel can be detected by using an operation to stop the electrically operated pump. This allows the viscosity of the fuel to be detected in preparation for a next start. Consequently, startability or a combustion state of the internal combustion engine can be improved.

According to the fifth invention, the viscosity of the fuel can be detected during operation of the electrically operated pump by changing the pressure setting value of the variable fuel pressure means. The viscosity of the fuel can therefore be detected regularly even while, for example, the internal combustion engine is operating normally. This improves accuracy in detecting the viscosity and in controlling to incorporate the detected viscosity. Additionally, there is no need to change a state of power supply to the electrically operated pump for changing the operating state of the pump. The pump is therefore less likely to receive influence of, for example, electric load fluctuations, allowing pump operation to be stabilized in a transient state.

According to the sixth invention, the notification means can notify a driver or the like of a vehicle that the viscosity of the fuel falls outside a reference range. This allows the driver or the like to learn quickly that the viscosity of the fuel is in an abnormal state and accordingly to take appropriate action.

BEST MODE OF CARRYING OUT THE INVENTION

First Embodiment
[Arrangements of the First Embodiment]

Figure 1:
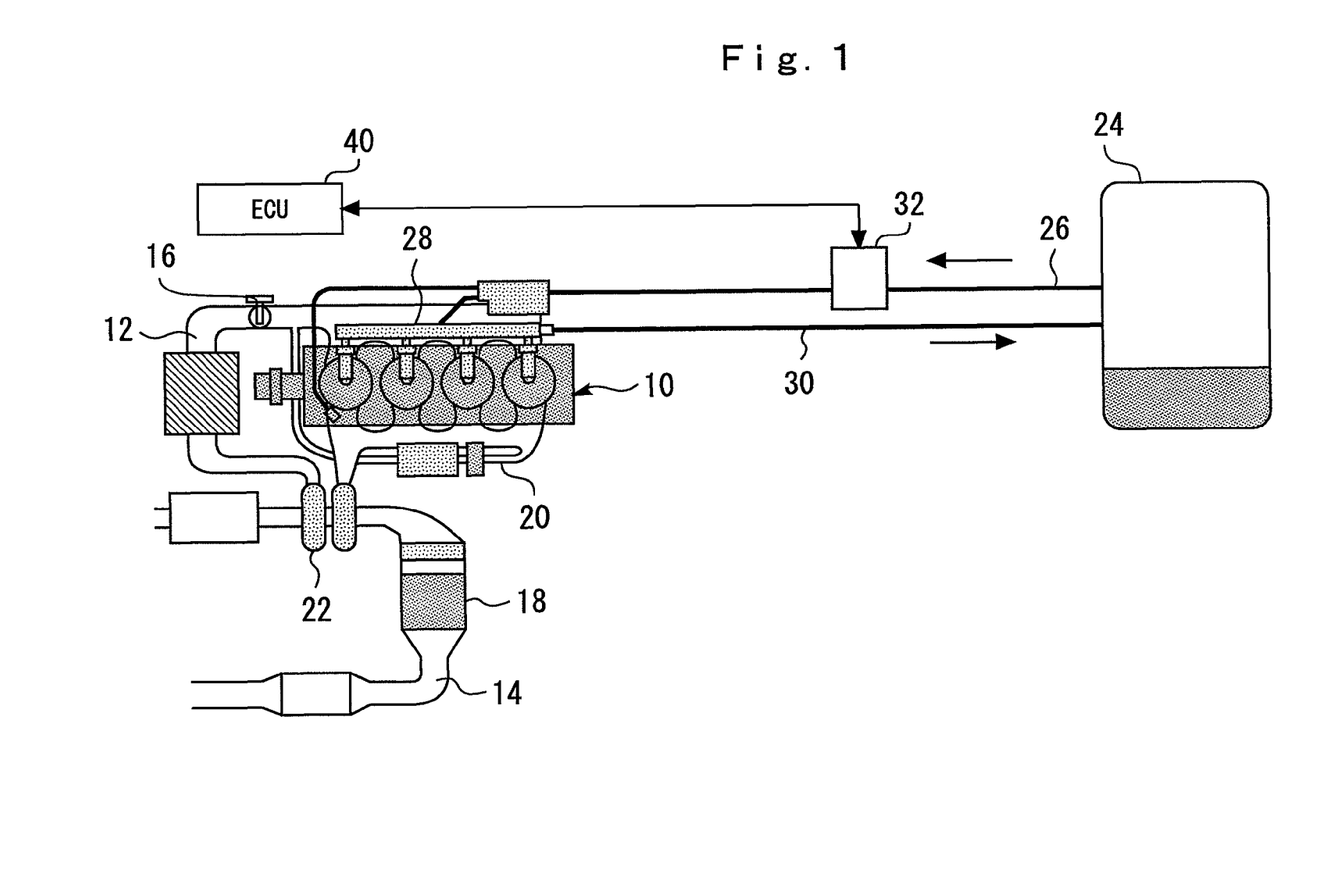
FIG. 1 is an illustration showing a general arrangement of a system according to the first embodiment of the present invention.

A first embodiment of the present invention will be described below with reference to FIG. 1. FIG. 1 is an illustration showing a general arrangement of a system according to the first embodiment of the present invention. The system according to this embodiment includes an internal combustion engine 10 formed, for example, from a diesel engine. The internal combustion engine 10 permits use of so-called biofuels, in addition to mineral fuels such as gasoline. Biofuels as the term is herein used refer to, for example, fuels having as a major component a plant oil of various kinds or alcohol produced using, for example, a plant material.

The internal combustion engine 10 includes an intake path 12 through which an intake air is drawn into each cylinder and an exhaust path 14 through which an exhaust gas is exhausted from each cylinder. The intake path 12 has an electronically controlled throttle valve 16 disposed therein and the exhaust path 14 has a catalyst 18 disposed therein. Specifically, the throttle valve 16 increases or decreases an intake air amount and the catalyst 18 purifies the exhaust gas. In addition, an EGR mechanism 20 and a turbocharger 22 are disposed between the intake path 12 and the exhaust path 14. Specifically, the EGR mechanism 20 recirculates part of the exhaust gas into an intake system and the turbocharger 22 supercharges the intake air by using an exhaust pressure. Additionally, each cylinder of the internal combustion engine 10 includes a fuel injection valve, an ignition plug, an intake valve, and an exhaust valve (none of these are shown).

A fuel system of the internal combustion engine 10 will be described below. The fuel system includes, for example, a fuel tank 24, a supply pipe 26, a common rail 28, and a return pipe 30. The supply pipe 26 is connected between the fuel tank 24 and an inflow side of the common rail 28 and functions to supply the common rail 28 with fuel, such as biofuel, stored in the fuel tank 24. In addition, the fuel injection valve of each cylinder is connected to the common rail 28, so that part of the fuel supplied to the common rail 28 is injected into each cylinder by the fuel injection valve. The return pipe 30, on the other hand, is connected between an outflow side of the common rail 28 and the fuel tank 24 and functions to return fuel that is an excess in the common rail 28 to the fuel tank 24.

Additionally, the supply pipe 26 includes a fuel pump 32 disposed therein. The fuel pump 32 delivers fuel drawn in from the side of the fuel tank 24 toward the common rail 28. The fuel pump 32 is an electrically operated pump driven by, for example, a general-purpose motor. The fuel pump 32 is operative according to a drive signal inputted to the motor by an ECU 40 to be described later. While the fuel pump 32 is operating, fuel delivered therefrom is supplied into the common rail 28, which increases a fuel pressure in the common rail 28. This fuel pressure is adjusted to a predetermined pressure by a pressure adjustment mechanism (not shown) disposed on an outflow side of the common rail 28 (or on the return pipe 30). Note that the arrangement depicted in FIG. 1 includes the fuel pump 32 disposed midway in the supply pipe 26. This is, however, not the only possible arrangement for the present invention; rather, for example, the fuel pump 32 may be disposed inside the fuel tank 24 and the supply pipe 26 connected to a delivery port of the pump.

The system of this embodiment, on the other hand, includes a sensor system having sensors of various types required for controlling a vehicle or the internal combustion engine and the ECU (electronic control unit) 40 for controlling an operating state of the internal combustion engine 10. The sensor system includes, for example, an air flow meter, a speed sensor, a coolant temperature sensor, and an air-fuel ratio sensor. Specifically, the air flow meter detects the intake air amount of the internal combustion engine. The speed sensor detects an engine speed. The coolant temperature sensor detects a coolant temperature of the internal combustion engine. The air-fuel ratio sensor detects an air-fuel ratio of the exhaust gas. These sensors are connected to an input side of the ECU 40.

Additionally, actuators of various types are connected to an output side of the ECU 40, including the fuel injection valve, the ignition plug, the EGR mechanism 20, and the fuel pump 32. The ECU 40, while detecting the operating state of the internal combustion engine using the sensor system, drives each of the actuators. Specifically, an injection amount and injection timing of fuel, ignition timing, and the like are set based on an output of the sensor system and, according to the settings, the actuators are driven.

In addition, the ECU 40 includes a pump control circuit that controls an output state of a drive signal (e.g. a drive voltage) to be outputted to the fuel pump 32 and a detection circuit that detects an actually flowing drive current according to the drive voltage. The ECU 40 further includes a memory circuit that stores a signal waveform of the drive current as time-series data. The ECU 40 performs a fuel viscosity detection control to be described below by using the foregoing circuits.

(Fuel Viscosity Detection Control)

The internal combustion engine 10 is formed from an engine that permits use of biofuels. Biofuels, however, tend to develop variations in viscosity because, for example, of a small difference in fuel components and to have viscosity gradually changing through deterioration with time such as oxidation. With variations in fuel viscosity, an error tends to occur in an actual injection amount in, for example, fuel injection control, even if the fuel injection valve is opened for a period of time corresponding to a target injection amount. Accordingly, this embodiment is arranged to detect viscosity of the fuel using the operation of the fuel pump 32.

A basic concept of the fuel viscosity detection control will first be described. In the fuel viscosity detection control, while the fuel pump 32 is operating in a certain steady state (a first steady state), an external factor that would change that steady state is applied to the fuel pump 32. Examples of the factor include: (1) changing the drive voltage of the pump; and (2) changing the delivery pressure (delivery load) of the pump. A period of time that elapses between a point in time when the above factor is applied and a point in time when the pump changes its state to a steady state different from that before (a second steady state) is then detected as a transition time. Note that the first and second steady states are set as two steady states, in which the fuel pump 32 outputs different output speeds.

While the fuel pump 32 is operating, a reaction force in accordance with the viscosity of the fuel acts on the pump. If, for example, a factor in a direction of an increasing output speed is applied, the higher the viscosity of the fuel, the longer the transition time between the two steady states. Specifically, if the viscosity is high, the motor of the fuel pump 32 becomes harder to rotate to make up for the higher viscosity, so that it takes longer for the output speed to build up to reach the steady state (specifically, for the drive current to become steady). If a factor in a direction of a decreasing output speed is applied, on the other hand, the higher the viscosity of the fuel, the faster the output speed decreases, resulting in a shorter transition time. In accordance with the fuel viscosity detection control, therefore, the viscosity of the fuel can be detected based on the above-described transition time.

Details of control of the first embodiment will next be described specifically. The first embodiment is arranged such that an application of the above-mentioned factor drive signal to the fuel pump 32 in a stationary state operates the pump in a steady operating state. The steady operating state as the term is herein used refers to a condition in which the drive current, the drive voltage, and the output speed of the fuel pump 32 are maintained at constant values compatible with an operation of the internal combustion engine. Specifically, in this embodiment, a condition in which the fuel pump 32 is stationary is the first steady state and a condition in which the pump is in the steady state operation is the second steady state. Then, the period of time that begins when the drive signal is outputted and ends when the fuel pump 32 enters the steady operating state is detected as the transition time.

Figure 2:
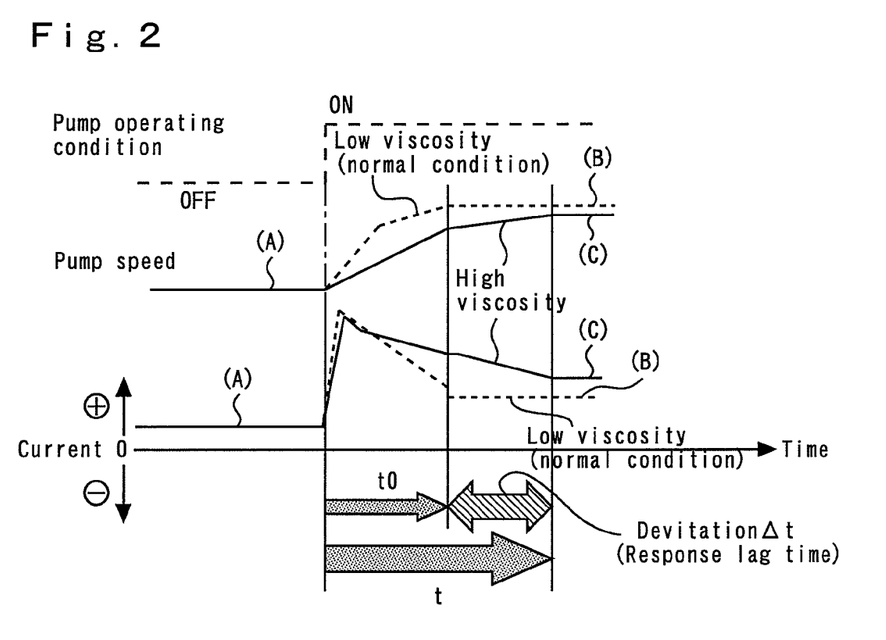
FIG. 2 is a diagram for illustrating the details of control in the first embodiment.

FIG. 2 is a diagram for illustrating the details of control in the first embodiment. The ECU 40 previously stores therein the transition time when the viscosity of the fuel is on a normal level as a reference time t0. (A) in FIG. 2 represents a condition in which the fuel pump 32 is stationary (where the drive current, the drive voltage, and the pump output speed are zero). If the drive signal is outputted from the ECU 40 to the fuel pump 32 in this condition, the pump starts to increase the output speed, which accompanies an increased drive current (pump load current).

When the fuel pump 32 enters the steady operating state, at least the drive current becomes a constant steady state value corresponding to the steady operating state. Timing at which the drive current becomes constant is detected by the ECU 40 as that at which the pump enters the steady operating state. Note that the steady state value may fluctuate depending on, for example, the viscosity of the fuel; however, the ECU 40 can detect the timing at which the drive current becomes constant as that of an entry in the steady operating state.

The ECU 40 then detects a transition time t that represents a period of time that begins when the drive signal is outputted and ends when the fuel pump 32 enters the steady operating state and calculates a deviation $\Delta t$ between the transition time t and the reference time t0 ($\Delta t = t - t0$). Note that, when the pump enters the steady operating state, not only the drive current, but the drive voltage, a drive electric power, and the pump output speed as well become constant steady state values. The present invention, therefore, only requires that the timing at which at least one of parameters of the drive voltage, the drive current, the drive electric power, and the output speed of the pump becomes a constant value be detected as the timing of the entry in the steady operating state and the parameter is not limited only to the drive current. Additionally, to detect the pump output speed, the speed is not necessarily be detected directly by, for example, a rotation sensor. Specifically, while the pump is operating, contact resistance of a moving part (e.g. a brush) of the motor changes, which causes the drive current or the drive voltage to fluctuate cyclically corresponding to the output speed. Accordingly, detection means of the present invention may be arranged so as to detect the output speed based on a fluctuation cycle of the drive current or the drive voltage.

Figure 3:
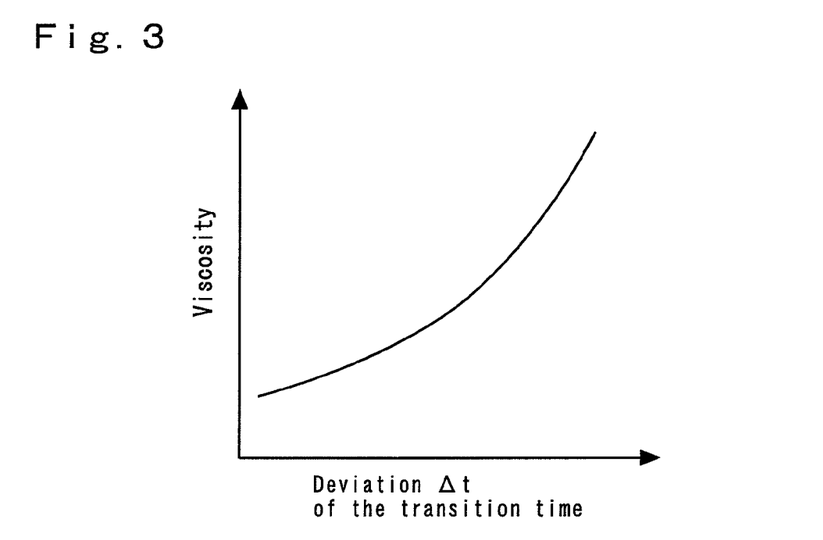
FIG. 3 is a characteristic curve representing a relationship between the deviation of the transition time and the fuel viscosity in the first embodiment of the present invention.

The abovementioned deviation Δt of the transition time represents time of a response lag in the pump output with reference to a case in which the viscosity of the fuel is on the normal level. If the viscosity is detected at the start of the fuel pump 32 as in this embodiment, the deviation Δt increases as the viscosity of the fuel becomes higher as shown in FIG. 3. FIG. 3 is a graph showing data representing this characteristic, specifically, a characteristic curve representing a relationship between the deviation of the transition time and the fuel viscosity in the first embodiment of the present invention. The characteristic data is previously stored in the ECU 40. The ECU 40 is therefore able to calculate the viscosity of the fuel by referring to the characteristic data of FIG. 3 based on the deviation Δt.

(Temperature Correction of Detected Viscosity)

Figure 4:
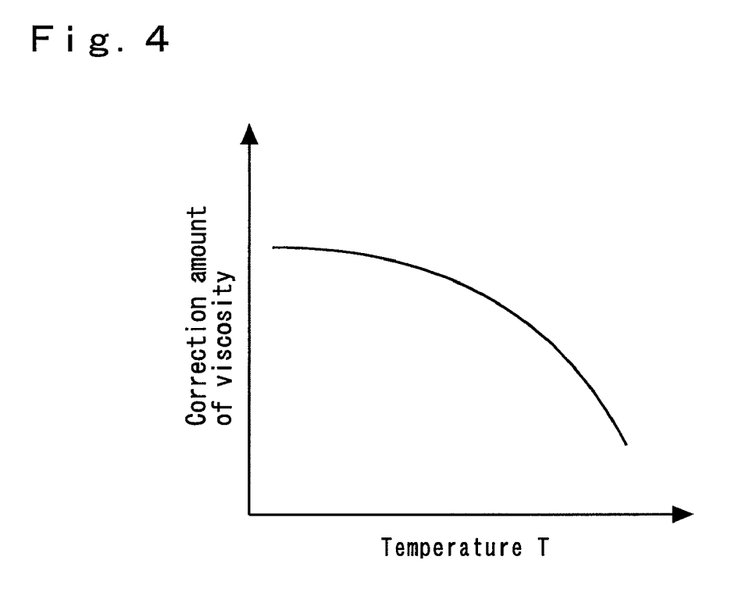
FIG. 4 is a characteristic curve showing a relationship between a fuel temperature and a viscosity correction amount.

The viscosity of the fuel also changes with temperature and, in this embodiment, the calculated value of the viscosity is subject to temperature correction. FIG. 4 is a characteristic curve showing a relationship between a fuel temperature and a viscosity correction amount. The characteristic data is previously stored in the ECU 40. The viscosity of the fuel generally decreases as the temperature increases, so that the viscosity correction amount is set so as to decrease as the temperature increases as shown in FIG. 4.

The ECU 40 determines the viscosity correction amount by referring to the characteristic data of FIG. 4 based on the fuel temperature. The viscosity correction amount is incorporated in the calculated value of the viscosity through, for example, integration means to thereby correct the calculated value according to the temperature. The fuel temperature used for the temperature correction process can be obtained through direct detection using, for example, a temperature sensor disposed in the fuel system or through estimation based on another temperature parameter (e.g. coolant temperature, lubricant temperature, or intake air temperature).

(Control Based on Fuel Viscosity)

Figure 5:
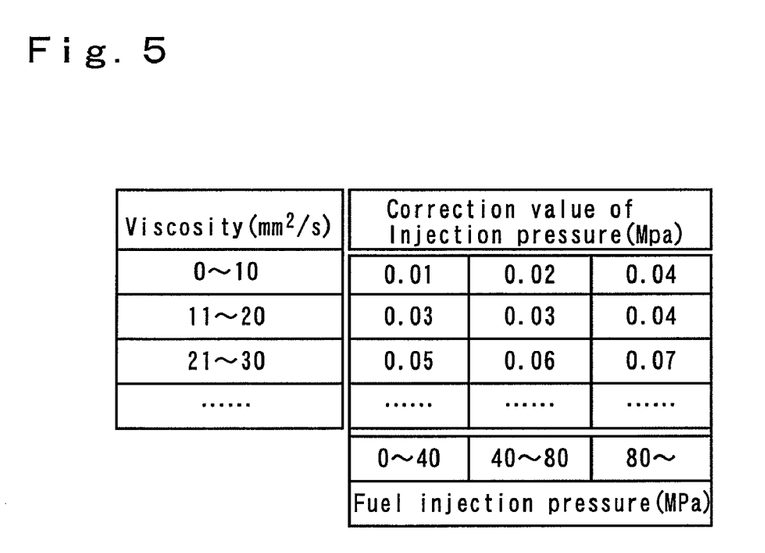
FIG. 5 is a data map showing a relationship between the viscosity of the fuel and an injection pressure correction value.

The viscosity of the fuel detected as described above is used, for example, for correction control of a fuel injection pressure. FIG. 5 is a data map showing a relationship between the viscosity of the fuel and an injection pressure correction value. The data map is a two-dimensional map for calculating the injection pressure correction value based on, for example, the viscosity of the fuel and the injection pressure and is previously stored in the ECU 40. The ECU 40 can obtain the injection pressure correction value according to the viscosity by referring to the data map of FIG. 5 based on the detected viscosity value and the fuel injection pressure described above. The output speed of the fuel pump 32 or the pressure adjustment mechanism are then controlled such that the fuel pressure in the common rail 28 is a target injection pressure in which the injection pressure correction value is incorporated. This allows the fuel injection pressure to be appropriately corrected at all times even with changing fuel viscosity values according to the change, so that the fuel injection amount can be accurately controlled.

(Fuel Viscosity Detection Control Performance Timing)

The above-described fuel viscosity detection control is performed each time the fuel pump 32 is started, specifically, the internal combustion engine is started. Consequently, even if the viscosity of the fuel changes due to, for example, parking for a long time, the latest viscosity at the start of the internal combustion engine can be detected and the detection result can be promptly incorporated in control of various kinds. In the present invention, an arrangement may still be made in which the fuel viscosity detection control is performed when the internal combustion engine (fuel pump) is stationary as shown in a second embodiment to be described later. Still another arrangement may combine the first and second embodiments, whereby the fuel viscosity detection control is performed at the start and stop.

(Fuel Viscosity Detection Control During Pump Operation)

In addition, an arrangement may be made in the present invention in which the viscosity is detected at any timing other than the start and stop of the fuel pump 32, specifically, during operation of the pump. More specifically, to detect the viscosity during operation of the pump, two steady states to be achieved during pump operation are previously set as first and second steady states. These steady states are defined as that in which at least one parameter of the drive voltage, drive current, drive electric power, and output speed of the pump is a steady state value different from each other.

Then, the deviation Δt of the transition time is detected, while the operating state of the fuel pump 32 is being changed from the first steady state to the second steady state by applying the abovementioned external factor during pump operation. This allows the viscosity of the fuel to be detected regularly even while, for example, the internal combustion engine is operating normally, thus enhancing the detection accuracy. An example of the factor to be applied during pump operation includes a voltage waveform of a drive signal being increased or decreased in a step fashion to the extent of not becoming zero. An arrangement is also possible in which the delivery pressure is switched during pump operation as shown in a third embodiment to be described later.

Further, in this embodiment, the first steady state and the second steady state are defined as having different pump output speeds. This is, however, not the only possible arrangement for the present invention; rather, the first and second steady states may be identical to each other. More specifically, in this case, the output speed is made to fluctuate by temporarily applying the abovementioned external factor to the fuel pump 32 that is operating in the constant steady state (=the first and second steady states). A period of time that begins with this point in time and ends when the pump operating state returns to an original steady state is then detected as the transition time. The viscosity of the fuel can also be detected by having such an arrangement.

[Specific Processes for Achieving the First Embodiment]

Figure 6:
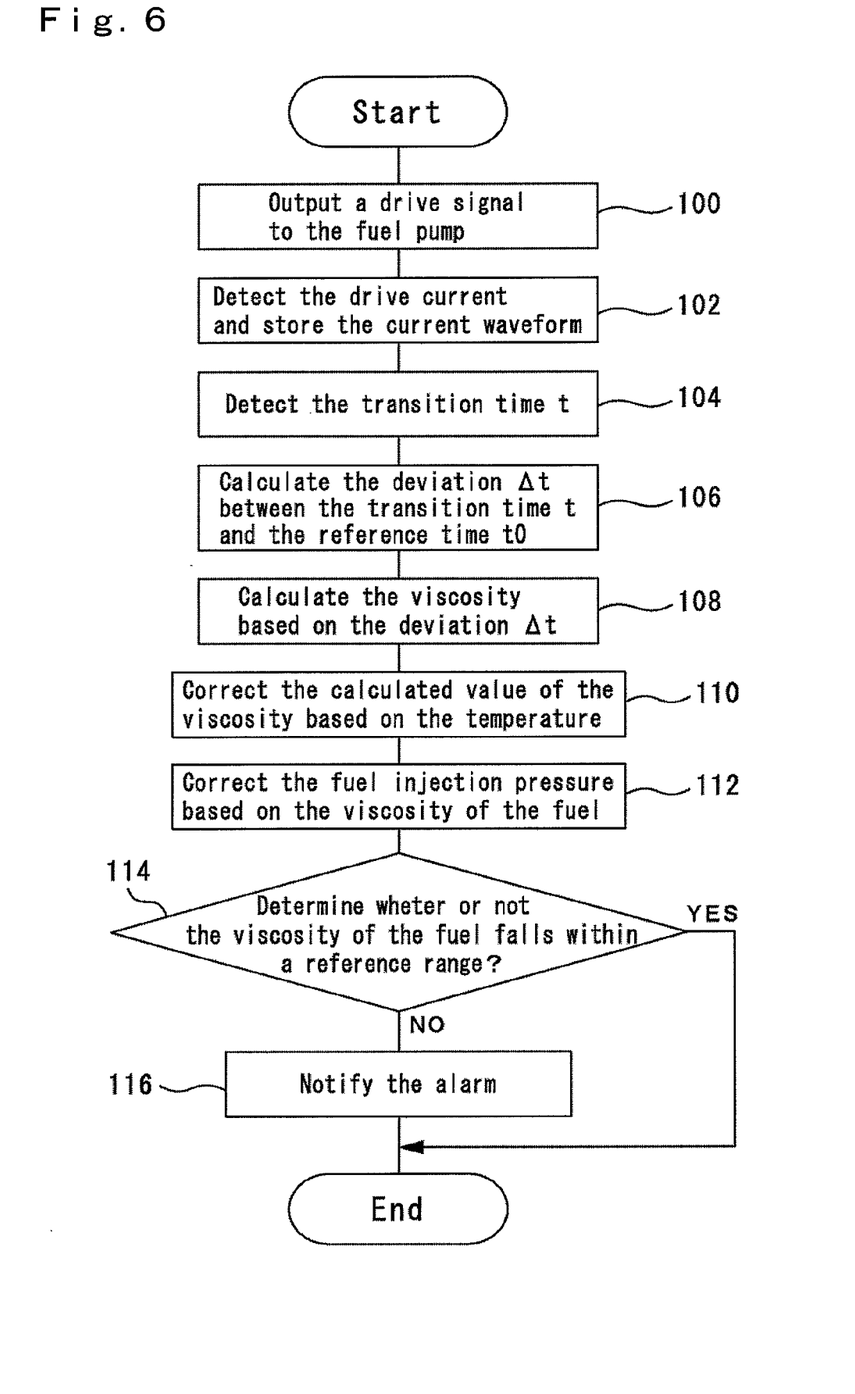
FIG. 6 is a flowchart showing the control performed by the ECU in the first embodiment of the present invention.

FIG. 6 is a flowchart showing the control performed by the ECU in the first embodiment of the present invention. In the routine shown in FIG. 6, a drive signal is outputted to the fuel pump 32 in a stationary state during, for example, the start of the internal combustion engine (step 100). This starts the fuel pump 32 and the fuel pump 32 then reaches the steady operating state. Meanwhile, the ECU 40 temporarily stores the waveform of the drive current as time-series data, while detecting the drive current during this period (step 102).

Based on this stored data, the transition time t that begins when the output of the drive signal is started and ends when the drive current reaches a constant state (steady state value) is detected (step 104) and, based on the transition time t and the reference time to, the deviation Δt is calculated (step 106). In step 104, preferably, not only the drive current, but also at least one of the parameters of the drive voltage, drive current, drive electric power, and output speed of the pump is detected and a period of time that begins when the output of the drive signal is started and ends when the parameter in question reaches a steady state value is detected as the transition time t.

The viscosity of the fuel is then calculated by referring to the characteristic data of FIG. 3 based on the deviation Δt (step 108). The calculated value of the viscosity is next corrected based on the temperature of the fuel as described earlier (step 110). Then, for example, the correction control of the fuel injection pressure described earlier is performed based on the viscosity after the correction (step 112).

In addition, the ECU 40 determines whether or not the viscosity of the fuel falls within a previously set reference range. If this determination is not true, a driver or the like of the vehicle is notified that the viscosity falls outside the reference range using means, for example, a buzzer, a lamp, voice, or a display change (steps 114, 116). This allows the driver or the like to learn quickly that the viscosity of the fuel is in an abnormal state, falling outside the reference range, so that appropriate action can be taken.

As described heretofore, according to this embodiment, the viscosity of the fuel can be accurately and easily detected by simply controlling the fuel pump 32 without having to install, for example, a viscosity sensor. The fuel pump 32 is an existing part in an ordinary fuel system. Consequently, in this embodiment, a viscosity detection system can be easily realized by simply adding the control without having to add any new part. This achieves a simplified system and cost reduction.

Additionally, in this embodiment, the viscosity can be detected by using the operation for starting the pump during, for example, the start of the internal combustion engine. Consequently, the latest viscosity can be highly accurately detected at all times during the start of operation even with a fuel whose viscosity tends to change easily, such as the biofuels and the detection result can be incorporated quickly for, for example, the control of the fuel injection pressure. This improves startability of the internal combustion engine and a combustion state immediately following the start.

Further, in this embodiment, the timing at which the drive current reaches the steady state value is detected as the timing at which the fuel pump 32 enters the steady state. This permits reliable detection of the pump entering the steady state without using, for example, a rotation sensor for detecting the pump speed. A simplified system and cost reduction can therefore be promoted.

Second Embodiment

A second embodiment of the present invention will be described below with reference to FIGS. 7 through 9. This embodiment incorporates substantially identical system arrangements (FIG. 1) as the first embodiment described above. This embodiment, however, differs from the first embodiment in that an arrangement is made so that the fuel viscosity detection control is performed at timing at which the fuel pump is stopped. Note that like or corresponding parts are identified in this embodiment by the same reference numerals as those used for the first embodiment described above and descriptions for those parts will be omitted.

[Features of the Second Embodiment]

The second embodiment is arranged so that the fuel pump 32 in a steady operating state is brought to a stop by turning off the drive signal as the factor described above. Specifically, in this embodiment, a condition in which the fuel pump 32 is operating steadily is defined as a first steady state and a condition in which the fuel pump 32 is stationary is defined as a second steady state. Then, a period of time that begins when the drive signal is turned off and ends when the fuel pump 32 becomes stationary is detected as the transition time.

Figure 7:
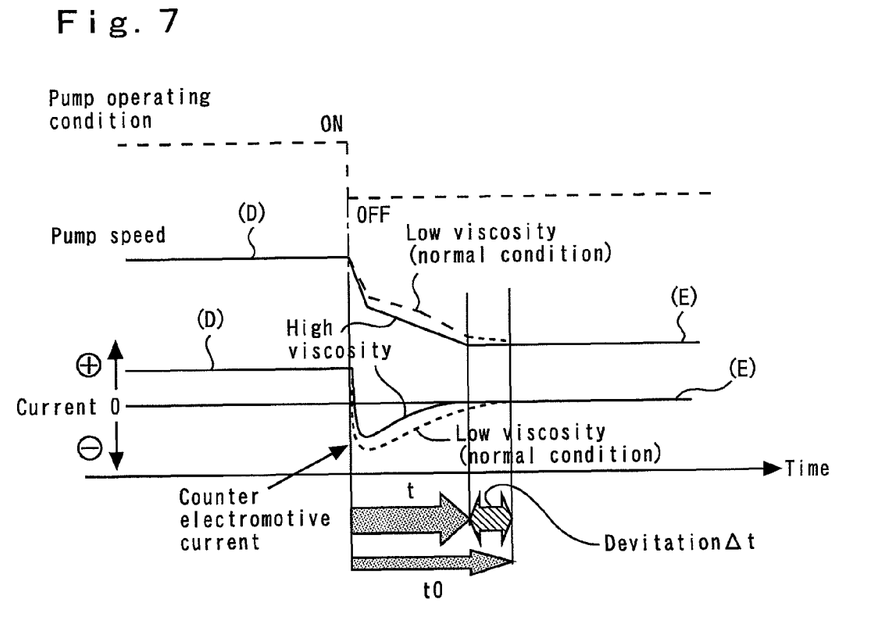
FIG. 7 is a diagram for illustrating details of control in the second embodiment.

FIG. 7 is a diagram for illustrating details of control in the second embodiment. (D) in FIG. 7 represents the steady operating state of the fuel pump 32. If the drive signal is turned off in this condition, a drive force of the motor driving the pump is lost, but the pump continues rotating for some time through an inertia force before stopping. During inertia rotation of the pump, a counter electromotive force (counter electromotive current) is generated in a motor coil. The counter electromotive current becomes zero when the inertia rotation of the pump stops as shown by (E) in FIG. 7. The ECU 40 detects the timing at which the counter electromotive current becomes zero as that at which the pump shifts to the stationary state.

The ECU 40 then detects the transition time t that begins when the drive signal is turned off and ends when the fuel pump 32 shifts to the stationary state and calculates the deviation Δt between the transition time t and the reference time t0. In the present invention, timing at which at least one of the parameters of the counter electromotive voltage, counter electromotive current, and output speed of the pump becomes zero has only to be detected as that of entry in the stationary state and this parameter is not limited to the counter electromotive current.

Figure 8:
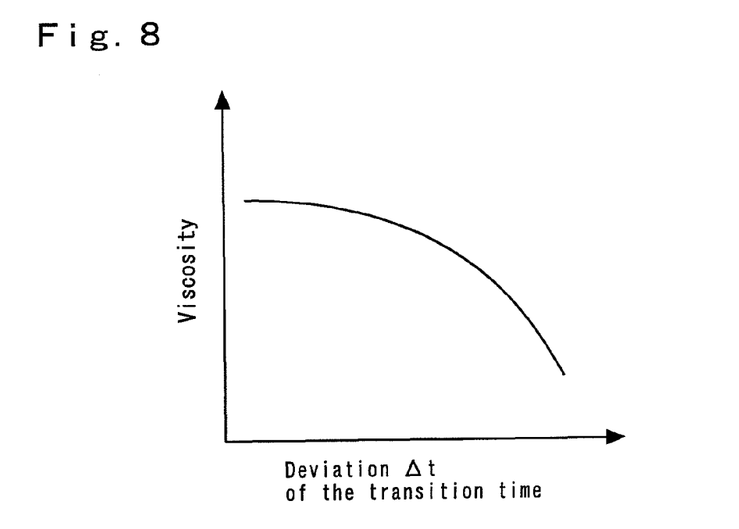
FIG. 8 is a characteristic curve representing a relationship between the deviation of the transition time and the fuel viscosity in the second embodiment of the present invention.

Because the inertia rotation of the fuel pump 32 opposes a reaction force received from the fuel, a period of time during which the inertia rotation continues tends to be shorter at higher viscosities of the fuel as shown in FIG. 8. FIG. 8 is a characteristic curve showing a relationship between the deviation in the transition time and the viscosity of the fuel in the second embodiment of the present invention. The characteristic data is previously stored in the ECU 40. As in the first embodiment, the ECU 40 can calculate the viscosity of the fuel by referring to the characteristic data of FIG. 8 based on the deviation Δt. Note that, in this embodiment, the ECU 40 may be mounted, for example, with a nonvolatile memory that retains data stored therein even when power is shut down, so that the viscosity of the fuel detected while the pump is stationary can be stored in this memory.

[Specific Processes for Achieving the Second Embodiment]

Figure 9:
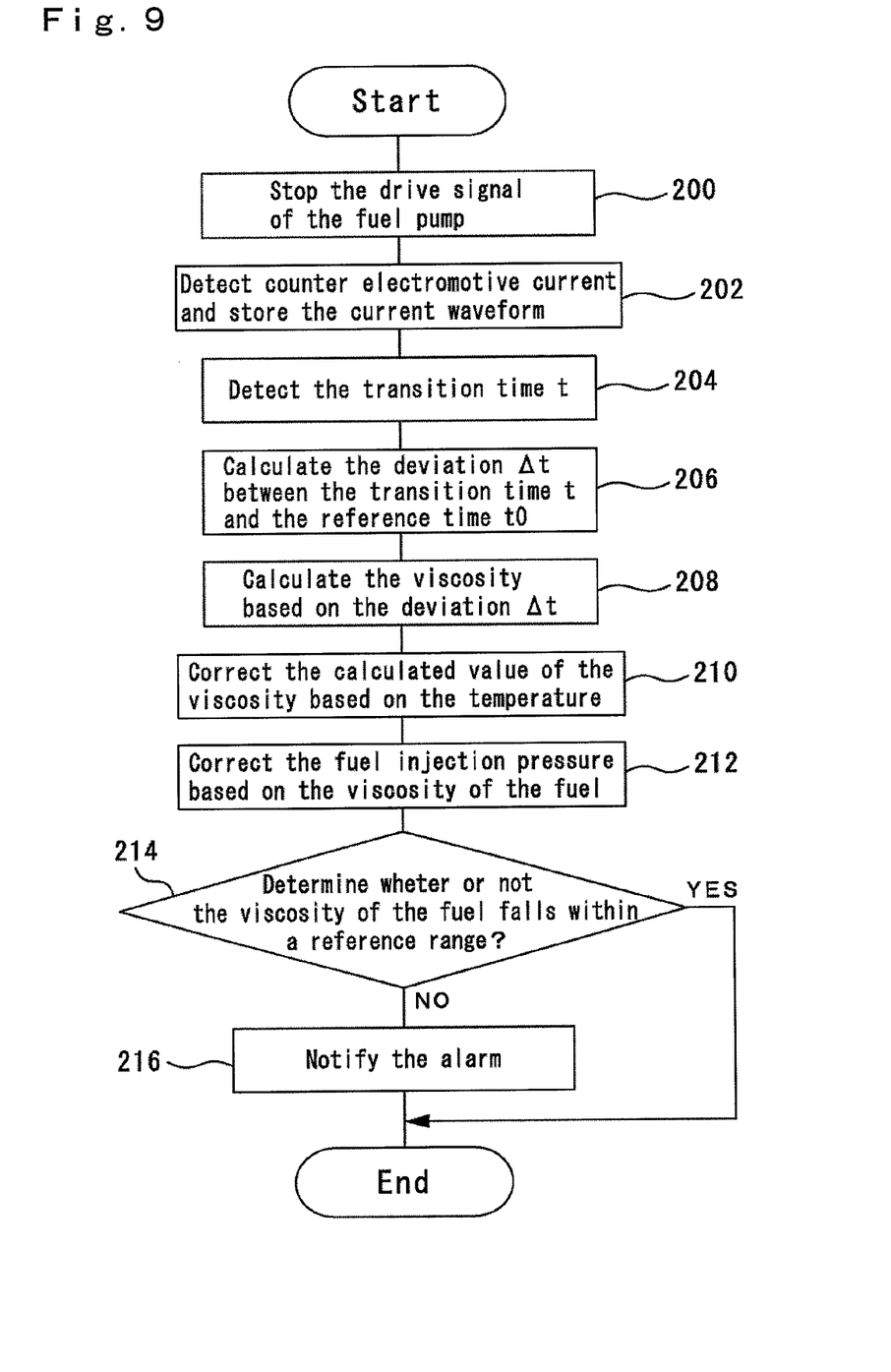
FIG. 9 is a flowchart showing the control performed by the ECU in the second embodiment of the present invention.

FIG. 9 is a flowchart showing the control performed by the ECU in the second embodiment of the present invention. In the routine shown in FIG. 9, the output of the drive signal is turned off relative to the fuel pump 32 in the steady operating state while, for example, the internal combustion engine is stationary (step 200). This brings the fuel pump 32 to a stop after a transient period. The ECU 40 stores in memory the waveform of the counter electromotive current, while detecting the counter electromotive current during the period (step 202). Then, in steps of from 204 through 216, the same processes as in steps of from 104 through 116 of the first embodiment described above are performed based on the stored data.

In this embodiment having arrangements as described above, too, substantially the same effects as the first embodiment described earlier can be obtained. Specifically, according to this embodiment, for example, the viscosity of the fuel can be detected for the next start when the internal combustion engine is to be stopped. Consequently, startability and combustion state of the internal combustion engine can be improved.

Third Embodiment

Figure 10:
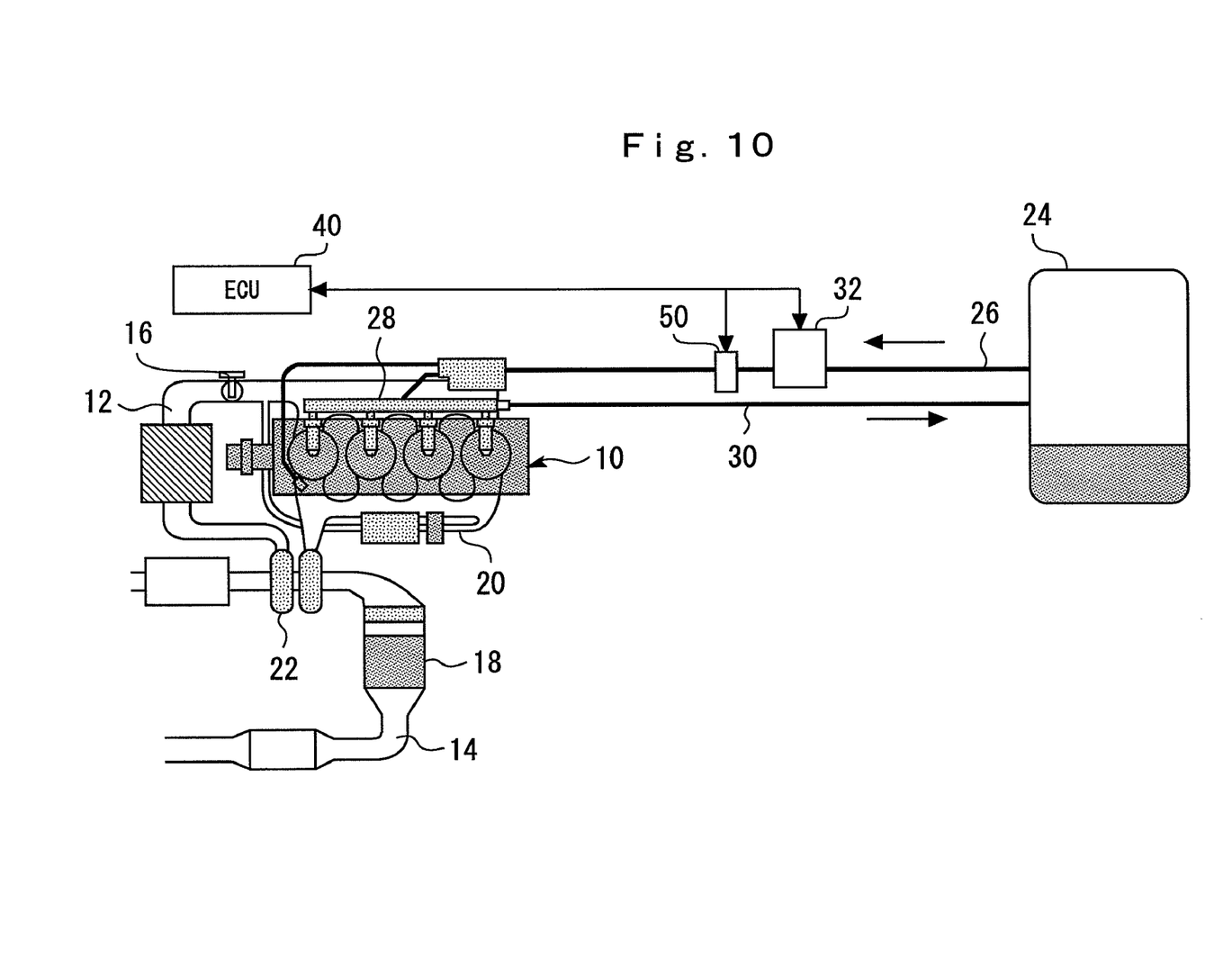
FIG. 10 is an illustration showing a general arrangement of a system according to the third embodiment of the present invention.

A third embodiment of the present invention will be described below with reference to FIGS. 10 and 11. FIG. 10 is an illustration showing a general arrangement of a system according to the third embodiment of the present invention. While incorporating substantially the same system arrangement as the first embodiment described earlier, this embodiment includes a pressure regulator 50 as variable fuel pressure means disposed on the delivery side of the fuel pump, in which the embodiment differs from the first embodiment. Note that like or corresponding parts are identified in this embodiment by the same reference numerals as those used for the first embodiment described above and descriptions for those parts will be omitted.

[Features of the Third Embodiment]

The pressure regulator 50 is capable of changing the pressure of the fuel delivered from the fuel pump 32 between at least two pressure setting values (hereinafter referred to as a high pressure and a low pressure). The pressure setting value is selected as controlled by the ECU 40. In this embodiment, relative to the fuel pump 32 that is operating in a certain steady operating state (a first steady state), the pressure setting value of the pressure regulator 50 is changed as the abovementioned external factor. This changes the delivery load of the pump, which causes the pump to enter a steady state different from before (a second steady state). The ECU 40 detects, at this time, a period of time that begins when the pressure setting value is changed and ends when the fuel pump 32 enters the second steady state as the above-described transition time. Note that this control allows the viscosity to be detected regardless of whether the pressure setting value is changed from the low pressure to the high pressure, or vice versa.

More specifically, if the pressure setting value is changed from the high pressure to the low pressure while the fuel pump 32 is operating, the delivery load of the pump decreases, so that the output speed (and the drive current) of the pump gradually increases, changing to a constant steady state that balances with the delivery load after the change of the setting. In this case, the transition time required for the output speed to increase is longer at higher viscosities of the fuel as in the first embodiment. The ECU 40 can therefore calculate the viscosity of the fuel based on the deviation Δt in the transition time by referring to the characteristic data having the same characteristics as the first embodiment (FIG. 3).

If the pressure setting value is changed from the low pressure to the high pressure while the pump is operating, on the other hand, the delivery load of the pump increases, so that the output speed of the pump gradually decreases toward the second steady state. In this case, the transition time required for the output speed to decrease is shorter at higher viscosities of the fuel as in the second embodiment described earlier. The ECU 40 can therefore calculate the viscosity based on the deviation Δt by referring to the characteristic data having the same characteristics as the second embodiment (FIG. 8).

[Specific Processes for Achieving the Third Embodiment]

Figure 11:
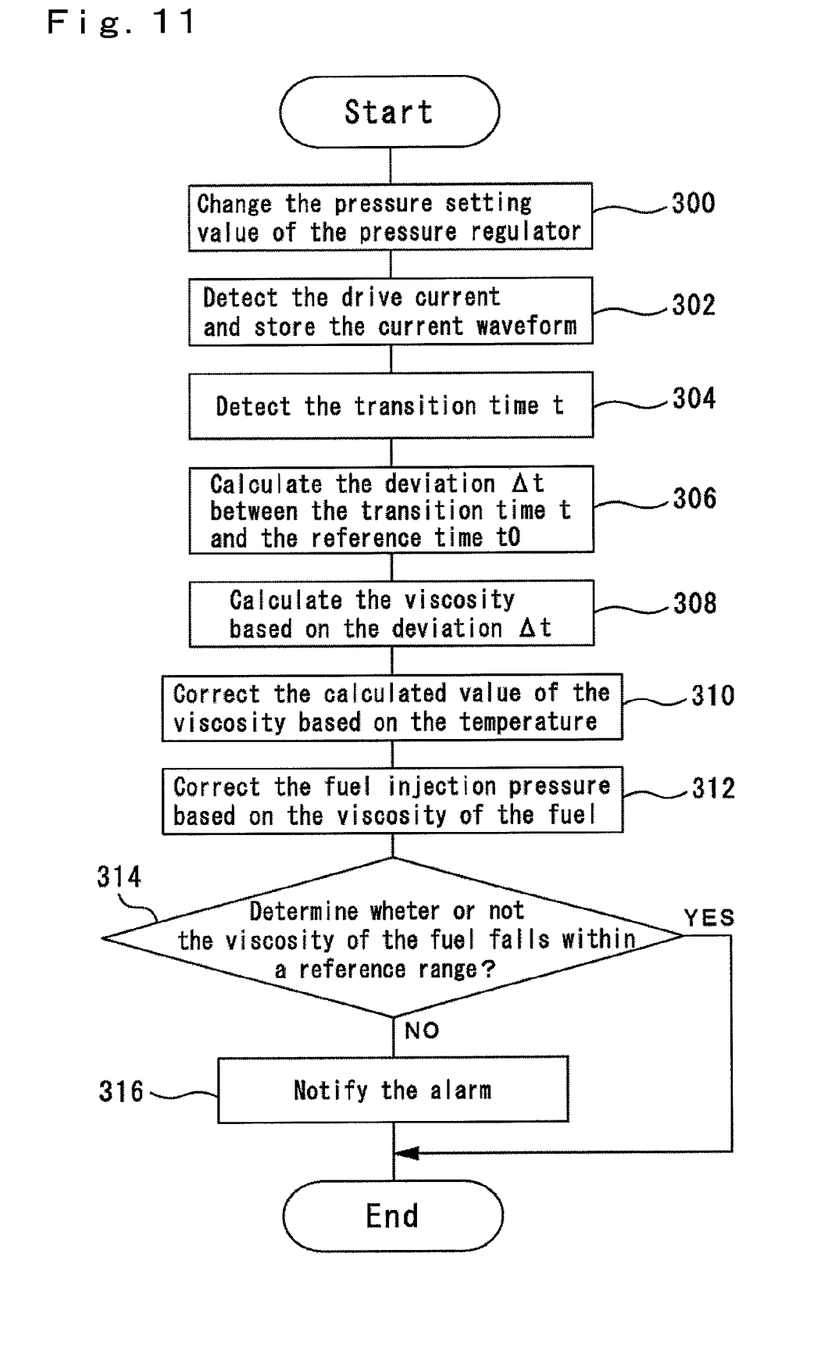
FIG. 11 is a flowchart showing the control performed by the ECU in the third embodiment of the present invention.

FIG. 11 is a flowchart showing the control performed by the ECU in the third embodiment of the present invention. The routine shown in this figure is repeatedly performed during operation of the internal combustion engine. In the routine shown in FIG. 11, the pressure setting value of the pressure regulator 50 is first changed relative to the fuel pump 32 that is in the steady operating state during operation of the internal combustion engine (step 300). This results in the fuel pump 32 entering a steady state that is different from that before by way of a transient period. The ECU 40 then stores the waveform of the drive current during this period (step 302). In steps of from 304 through 316, the same processes as in steps of from 104 through 116 of the first embodiment described earlier are performed based on this stored data.

In this embodiment having arrangements as described above, too, substantially the same effects as the first embodiment described earlier can be obtained. In this embodiment, in particular, the viscosity of the fuel can be detected while the fuel pump 32 is operating by changing the pressure setting value of the pressure regulator 50. This allows the viscosity of the fuel to be detected regularly even while, for example, the internal combustion engine is operating normally, thus improving accuracy in detecting the viscosity and in controlling to incorporate the detected viscosity. In addition, there is no need to change a state of power supply to the fuel pump 32 for changing the operating state of the pump. Consequently, the pump is less likely to receive influence of, for example, electric load fluctuations, allowing pump operation to be stabilized in a transient state.

In the first embodiment described earlier, step 100 in FIG. 6 represents a specific example of operating state change means (pump start means) and step 104 represents a specific example of transition time detection means (start time detection means). In the second embodiment, step 200 in FIG. 9 represents a specific example of operating state change means (pump stop means) and step 204 represents a specific example of transition time detection means (stop time detection means). Additionally, in the third embodiment, step 300 in FIG. 11 represents a specific example of operating state change means and step 304 represents a specific example of transition time detection means. Similarly, in FIGS. 6, 9, and 11, steps 102, 202, and 302 represent specific examples of detection means, steps 108, 208, and 308 represent specific examples of viscosity calculation means, and steps 116, 216, and 316 represent specific examples of notification means.

The embodiments have been described for an example case in which the fuel pump 32 is used to detect the viscosity of the fuel. The fuel pump is not necessarily used for the present invention; rather, an arrangement may be made in which an electrically operated pump of another type may be used to detect the viscosity. One example is a detection pump disposed in the fuel system, in addition to the fuel pump, and the detection pump is used for detecting the viscosity.

The embodiments have also been described for an example case in which the viscosity of the biofuel is detected. This is, however, not the only possible application of the present invention. The present invention may be widely applied to fuels of various types including, for example, gasoline, alcohol fuel, and light oil.

Description of Reference Numerals 10 internal combustion engine, 12 intake path, 14 exhaust path, 16 throttle valve, 18 catalyst, 20 EGR mechanism, 22 turbocharger, 24 fuel tank, 26 supply pipe, 28 common rail, 30 return pipe, 32 fuel pump (electrically operated pump), 40 ECU (electronic control unit), 50 pressure regulator (variable fuel pressure means)

The invention claimed is:

1. A fuel viscosity detection apparatus comprising:
an electrically operated pump for drawing and delivering fuel;
operating state change means for applying to the electrically operated pump a factor for changing an operating state of the electrically operated pump from a first steady state to a second steady state;
transition time detection means for detecting a period of time that begins when the factor is applied to the electrically operated pump and ends when an actual operating state becomes the second steady state as a transition time between the steady states; and
viscosity calculation means for calculating a viscosity of the fuel based on the transition time.

2. The fuel viscosity detection apparatus according to claim 1, further comprising:

detection means for detecting at least one of parameters of current, voltage, and electric power supplied to the electrically operated pump and an output speed of the electrically operated pump,
wherein the transition time detection means detects a period of time that begins when the factor is applied to the electrically operated pump and ends when the parameter becomes a value associated with the second steady state as the transition time.

3. The fuel viscosity detection apparatus according to claim 1,
wherein the operating state change means includes pump start means for changing the operating state of the electrically operated pump from a stationary state that is the first steady state to a steady operating state that is the second steady state by outputting a drive signal to the electrically operated pump; and
the transition time detection means includes start time detection means for detecting a period of time that begins when the drive signal is outputted and ends when the electrically operated pump enters the steady operating state as the transition time.

4. The fuel viscosity detection apparatus according to claim 1,
wherein the operating state change means includes pump stop means for changing the operating state of the electrically operated pump from a steady operating state that is the first steady state to a stationary state that is the second steady state by turning off the drive signal to the electrically operated pump; and
the transition time detection means includes stop time detection means for detecting a period of time that begins when the drive signal is turned off and ends when the electrically operated pump stops as the transition time.

5. The fuel viscosity detection apparatus according to claim 1, further comprising:
variable fuel pressure means for variably setting a pressure of the fuel delivered from the electrically operated pump,
wherein the operating state change means changes the operating state of the electrically operated pump from the first steady state to the second steady state by changing a pressure setting value of the variable fuel pressure means; and
the transition time detection means detects a period of time that begins when the pressure setting value is changed and ends when the electrically operated pump enters the second steady state as the transition time.

6. The fuel viscosity detection apparatus according to claim 1, further comprising:
notification means for notifying a state in which the viscosity of the fuel falls outside a predetermined reference range.

* * * * *